US005797404A

United States Patent [19]

[11] Patent Number: 5,797,404

[45] Date of Patent: Aug. 25, 1998

Stanchin, II

[54] DISPOSABLE HANDCUFF

[76] Inventor: Emery John Stanchin, II, 9617 Yarmouth Ct., Louisville, Ky. 40272

[21] Appl. No.: 591,928

[22] Filed: Jan. 29, 1996

Related U.S. Application Data

[63] Continuation-in-part of Ser. No. 26,479, Jul. 29, 1994, Pat. No. Des. 366,733.

[51] Int. Cl.[6] .................... A61B 19/00

[52] U.S. Cl. .................... 128/869; 128/878; 128/879; 70/16; 24/16 PB

[58] Field of Search .................... 128/869, 878, 128/879, 880; 70/16; 24/16 PB

[56] References Cited

U.S. PATENT DOCUMENTS

| | | | |
|---|---|---|---|
| D. 364,038 | 11/1995 | Stanchin . | |
| 4,071,023 | 1/1978 | Gregory . | |
| 4,572,466 | 2/1986 | Yamaguchi | 24/16 PB |
| 4,854,138 | 8/1989 | Charland . | |
| 4,909,051 | 3/1990 | Lee . | |
| 4,964,419 | 10/1990 | Karriker . | |
| 5,083,346 | 1/1992 | Orton | 24/16 PB |
| 5,088,158 | 2/1992 | Burkholder . | |
| 5,159,728 | 11/1992 | Bingold . | |
| 5,193,254 | 3/1993 | Geisinger . | |
| 5,354,021 | 10/1994 | Farrell | 24/16 PB |
| 5,524,463 | 6/1996 | Schenkel | 24/16 PB |

*Primary Examiner*—Michael A. Brown

*Attorney, Agent, or Firm*—Middleton & Reutlinger; David W. Carrithers

[57] ABSTRACT

A disposable handcuff providing a two loop expandable strap restraint for law enforcement formed from a continuous single foldable strap that is light weight, strong, inexpensive, disposable, and can be formed of readily available and readily obtainable materials.

11 Claims, 2 Drawing Sheets

DISPOSABLE HANDCUFF

This application is a continuation in part of application Ser. No. 29/026,479 filed on Jul. 29 1994,now U.S. Pat. No. D. 366,733.

BACKGROUND OF THE INVENTION

Law enforcement personnel normally carry only one set of metal handcuffs, or simple plastic straps such as set forth in U.S. Pat. No. 5,193,254 by Geisinger. Conventional metal handcuffs are inconvenient, cumbersome, and require cooperating keys, which may or may not be readily available and shared by several officers in various locations. The single strap such as disclosed in U.S. Pat. No. 5,193,254 may be used to wrap around a retainee's wrists; however, it is difficult to pull the strap tight enough to secure the retainee without cutting the wrists, and if too loose, the retainee can wiggle the wrists free from the single looped or single twisted strap cuffs. U.S. Pat. No. 5,159,728 discloses a double loop strap restraint; however, the device requires a specially designed strap having spaced apart heads, whereby the tips of the straps must be placed in the heads carefully and pulled thereby requiring the use of both hands of the officer. Moreover, the loops are spaced apart from one another and appear to require considerable time to use, which is not always a luxury which an officer is afforded when using restraining devices. Another double loop restraining device is set forth in U.S. Pat. No. 5,088,158 which also utilizes a special head having two apertures therethrough.

SUMMARY OF THE INVENTION

The instant application relates to disposable double loop handcuffs formed from a single plastic strap having locking heads which may be folded when not in use and expanded and tightened around the wearer to become form fitting versatile disposable restraints. More particularly, it relates to self-clinching disposable plastic straps terminating in a locking head into which the tip of the strap is inserted and pulled through in a ratchet and pawl arrangement for locking in place used in combination with a separating slip ring and elastomer retaining means for packaging.

More particularly, the present invention provides a disposable cuff for providing a double loop restraining device from a single strap having a ring, an elongated strap having a first tip end and a second locking head end locked in cooperative engagement forming a loop. Wherein the loop is flattened for insertion through the ring to a selected position and folded around the ring. A means such as an elastomeric ring or band is used for releasably holding the loop in a folded position around the ring. Wherein pulling on the opposing ends of the loop results in the elastomer band being snapped over the ring forming a pair of strap loops separated by a ring. Upon pulling the retainees hands through the strap loops, the strap loops are self-tightening through the pulling of the tip end of the strap.

BRIEF DESCRIPTION OF THE DRAWINGS

A better understanding of the present invention will be had upon reference to the following description in conjunction with the accompanying drawings in which like numerals refer to like parts throughout the several views and wherein.

SPECIFICATION

Figure 1:
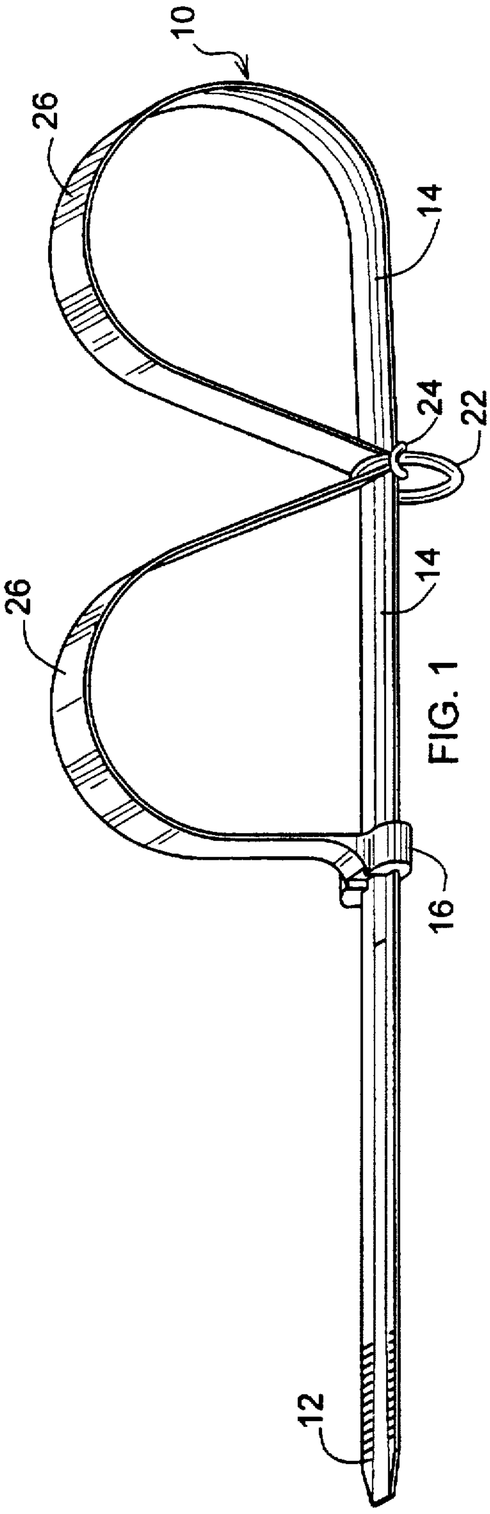
FIG. 1 is a perspective view of a handcuff made showing the present invention.
Figure 3:
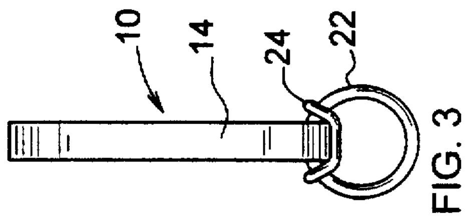
FIG. 3 is elevational right end view thereof.
Figure 2:
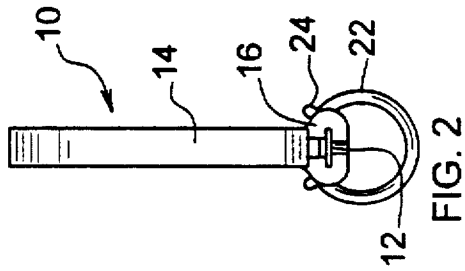
FIG. 2 is a elevational left end view thereof.

The disposable handcuff lamp bar of the present invention is manufactured from readily available materials and simple in design. The preferred strap embodiment is comprised of plastic, more particularly nylon due to its light weight and great structural strength. The separating slip ring is formed from steel, and the retaining ring means is formed from an elastomer such as an "O-ring" or rubber band. It is contemplated that the strap may be formed from plastic, such as high density polyethylene, nylon, PVC, or a polymer composite containing graphite or aramid fibers could be used in combination with or substituted for the nylon or metal components of the present invention.

Referring now to the drawings, FIGS. 1–6 the present invention utilizes simple plastic straps utilizing a ratchet and pawl arrangement such as described and shown in U.S. Pat. No. 5,193,254 by Geisinger hereby incorporated by reference.

Figure 4:
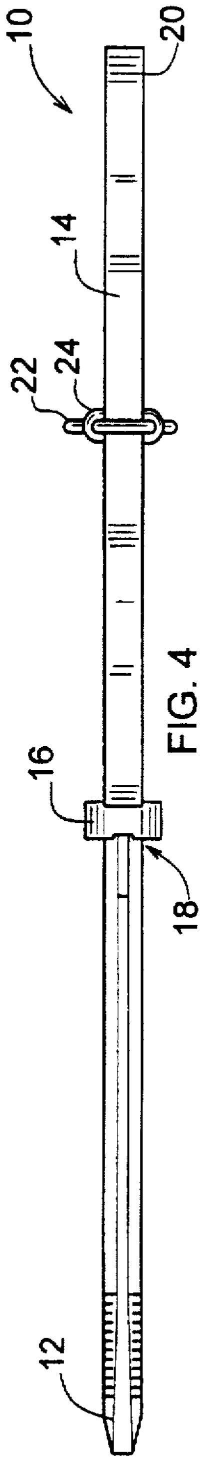
FIG. 4 is top plan view thereof.
Figure 5:
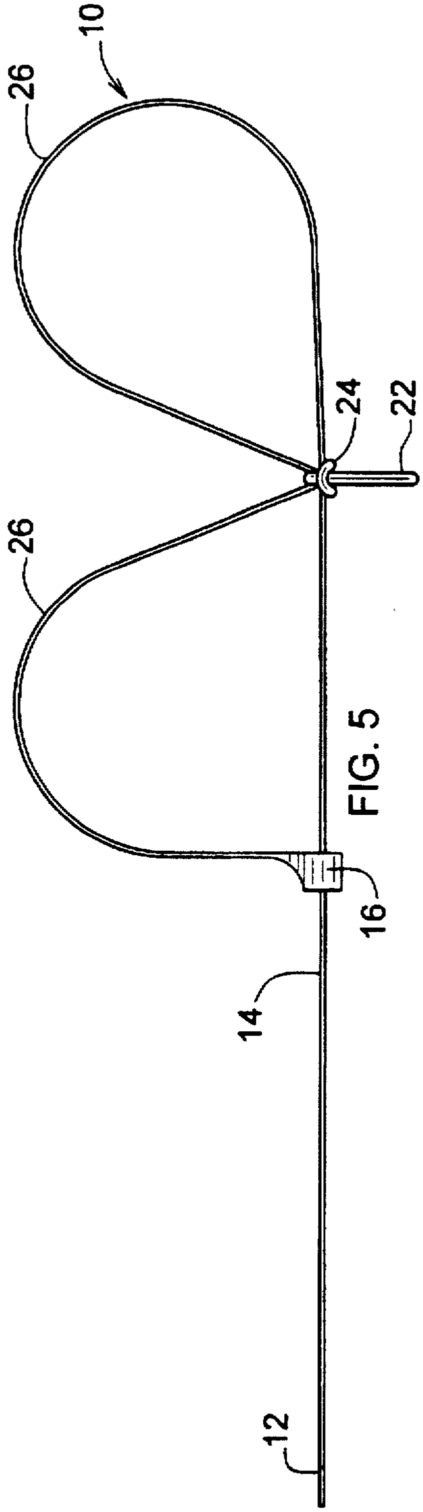
FIG. 5 is a front elevational view, the rear being a mirror image thereof.
Figure 6:
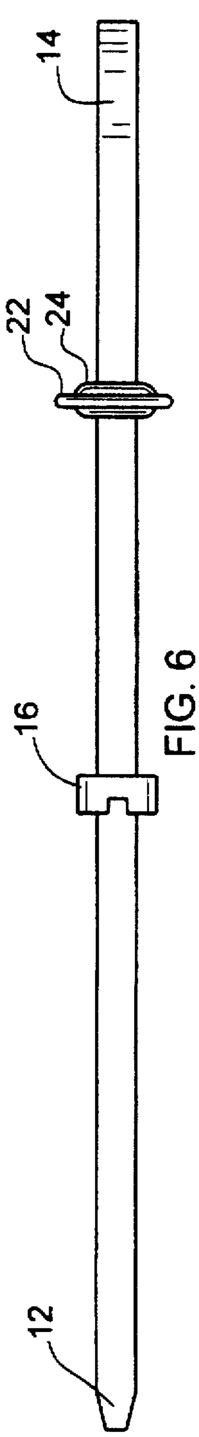
FIG. 6 is a bottom plan view thereof.

The disposable handcuffs 10 of the present invention, are formed by inserting the distal end or tip 12 or a strap 14 through the terminal locking head 16 forming a loop. As best shown in FIG. 4, the loop is flattened having the tip 12 and head 16 at one first end 18 and a fold at the opposite end 20, at least enough to insert a ring 22 of a selected size over the selected end thereof. The ring 22 is slipped over the loop and spaced at a selected position generally at about the center of the loop. The first tip end 18 and second locking head end 20 of the loop are brought together and folded about the ring 22. A retaining means 24 such as an elastomer is slipped over and around the ring 22, (or over the folded loop), holding the strap 14 into the folded storage position centered on both sides of the ring 22; thereby revealing an open loop portion of the ring 22 at the top for grasping. An elastomeric material such as an "O-ring" is used as a retaining means in the preferred embodiment for biasing the upper center portion of the loop and the lower portion of the ring 22 together; however, it is contemplated that a rubber band or other flexible or breakaway material may be utilized therefor.

The folded disposable cuff 10 may be stored in a shirt pocket, trouser pocket, or a pouch such as is described in U.S. Pat. No. D364,038, hereby incorporated by reference.

To use the disposable handcuff 10, simply pull a disposable handcuff 10 from the storage pouch or pocket. Grab hold of the first end 18 and the second end 20 with each hand, and pull. Assembly of the disposable cuff 10 is such that the retaining means 24 holds the loop folded around the ring 22 together under tension due to the memory of the plastic in the strap 10. Upon pulling with only a little effort, the elastomer retaining means 24 will be biased over the ring 22 by the tension provided by the bending of the strap 14 and snap over the ring 22 effortlessly, or break the retaining means 24, whereby the retainee's hands may be placed through the double strap loops 26 formed and separated by the ring 22. The first tip end 18 is then pulled and the rachet and pawl cooperates to tighten the loops around both wrists of the retainee at the same time with a single motion.

Moreover, a pair of small pliers may be utilized in a pouch kit for releasing the retainee at the desired time at any location, whereby the disposable cuff 10 may be discarded at the officer's convenience.

The foregoing detailed description is given primarily for clearness of understanding and no unnecessary limitations are to be understood therefrom, for modifications will become obvious to those skilled in the art based upon more recent disclosures and may be made without departing from the spirit of the invention and scope of the appended claims.

I claim:

1. A disposable cuff for providing a double loop restraining device from a single strap, comprising:

means for separating and holding having an aperture therethrough;

an elongated flexible strap having a tip end and a unidirectional locking head end, said flexible strap being inserted through said locking head end locking in sliding cooperative engagement therewith forming a first loop, said first loop being substantially flattened for insertion through said aperture of said means for separating and holding to a selected position forming a second loop of reduced diameter and a third loop of reduced diameter extending on each side of said means for separating and holding;

removable retaining means for biasing said flexible strap against a side of said means for separating and holding;

whereby inserting a first object through said second loop, and inserting a second object through said third loop, and pulling on said tip end of said flexible elongated strip slides said flexible elongated strip through said locking head and though said means for separating and holding contracting said second loop around said first object and simultaneously contracting said third loop around said second object holding said first object and said second object securely on opposing sides of said means for separating and holding.

2. The disposable cuff of claim 1, wherein said removable retaining means is an elastomer band of smaller diameter than said ring.

3. The disposable cuff of claim 1, wherein said removable retaining means is expandable.

4. The disposable cuff of claim 1, wherein said first means for holding is a ring.

5. The disposable cuff of claim 1, said removable retaining means being stretched and snapped over said means for holding and separating, said removable retaining means being retained between said means for holding and separating and said flexible strap.

6. The disposable cuff of claim 1, wherein said removable retaining means is an "O-ring".

7. The disposable cuff of claim 1, wherein said flexible strip comprises high density polyethylene, nylon, PVC, metal, a polymer composite containing graphite fibers, and combinations thereof.

8. The disposable cuff of claim 1, wherein said removable retaining means comprises break-away material.

9. The disposable cuff of claim 1, wherein said removable retaining means is flexible.

10. The disposable cuff of claim 1, wherein said removable retaining means releasably holds said first loop in a folded position around said means for separating and holding so that said second loop and said third loop are adjacent one another.

11. The disposable cuff of claim 1, wherein said removable retaining means is a rubber band.

* * * * *